United States Patent
Williamson et al.

(10) Patent No.: US 6,294,572 B1
(45) Date of Patent: Sep. 25, 2001

(54) CRYSTALLINE N-ACETYL NEURAMINIC ACID DERIVATIVES AND PROCESS FOR THEIR PREPARATION

(75) Inventors: Christopher Williamson; William James White; Vipulkumar Patel, all of Stevenage (GB)

(73) Assignee: Biota Scientific Management Pty Ltd., Glen Iris (AU)

( * ) Notice: Subject to any disclaimer, the term of this patent is extended or adjusted under 35 U.S.C. 154(b) by 0 days.

(21) Appl. No.: 09/346,583

(22) Filed: Jul. 2, 1999

Related U.S. Application Data

(63) Continuation of application No. 08/652,594, filed as application No. PCT/EP94/04154 on Dec. 15, 1994, now abandoned.

(30) Foreign Application Priority Data

Dec. 17, 1993 (GB) .................................................. 9325841

(51) Int. Cl.$^7$ ....................... A61K 31/351; C07D 309/28
(52) U.S. Cl. ............................................. 514/459; 549/424
(58) Field of Search .............................. 549/424; 514/459

(56) References Cited

U.S. PATENT DOCUMENTS 5,639,786    6/1997   Von Itzstein et al. ............... 514/459

FOREIGN PATENT DOCUMENTS

91/16320    10/1991   (WO) .

*Primary Examiner*—Laura L. Stockton
(74) *Attorney, Agent, or Firm*—Foley & Lardner

(57) ABSTRACT

Two useful crystal hydrates of 5-acetamido-2,3,4,5-tetradeoxy-4-guanidino-D-glycero-D-galacto-non-2-enopyranosonic acid have either a low or high aspect ratio. These crystalline N-acetyl neurominic acid derivatives are favored for pharmaceutical formulation because of their physical properties. For example, the low aspect ratio crystal has good flow properties, and the high aspect ratio crystal has a stable water content over time.

32 Claims, No Drawings

CRYSTALLINE N-ACETYL NEURAMINIC ACID DERIVATIVES AND PROCESS FOR THEIR PREPARATION

This application is a continuation of application Ser. No. 08/652,594, filed Nov. 21, 1996, now abandoned which is a national stage of PCT/EP94/04154 filed Dec. 15, 1994.

BACKGROUND OF THE INVENTION

1. Field of the Invention

The present invention relates to derivatives of N-acetl neuraminic acid and their use in medicine. More particularly the invention is concerned with particular physical forms of 5-acetamido-2,3,4,5-tetradeoxy-4-guanidino-D-glycero-D-galacto-non-2enopyranosonic acid (the 4-guanidino analogue of DANA; also known as 5-(acetylamino)-2,6 andydro-3,4,5-trideoxy-4-guanidino-D-glycereo-D-galacto-non-2-enonic acid), pharmaceutical formulations thereof and their use in therapy.

2. Description of Related Art

PCT/AU91/00161 (publication no. WO91/16320) describes a number of derivatives of 5-acetamidino-2,3,5-trideoxy-D-glycero-D-galacto-non-2-enopyranosonic acid (2,3,-dideoxy-2,3-didehydro-N-acetyl-neuraminic acid; DANA) including the 4-guanidino analogue of DANA. The 4-guanidino analogue of DANA is prepared by the reaction of the corresponding O-acyl protected 4-amino analogue of DANA by reaction with S-methylisourea followed by deprotection, purification by chromatography and freeze-drying.

The structure of the 4-guanidino analogue of DANA is shown below:

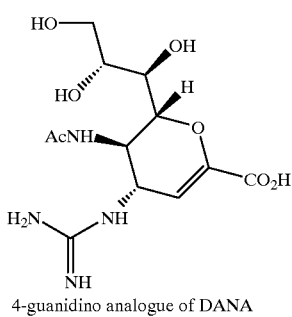

4-guanidino analogue of DANA

We have now found that the compound of formula (1) can be obtained in crystalline form.

SUMMARY OF THE INVENTION

There is thus provided in a first aspect of the invention 5-acetamido-2,3,4,5-tetradeoxy-4guanidino-D-glycero-D-glacto-non-2enopyramosonic acid in crystalline form.

We have further found that the compound of formula (I) may be obtained by crystallisation under certain conditions in the form of a crystalline hydrate (hereinafter Hydrate I). Hydrate I exists in the form of crystals having a low aspect ratio, for example, tabular crystals, which are favoured for pharmaceutical formulation because of their physical properties, e.g. good flow characteristics. The water content of Hydrate I is related to relative humidity (RH). Water uptake of Hydrate I varies from zero at RH of 0% up to 10% at RH of 90–100%.

The compound of formula (I) may also be crystallised in the form of dihydrate (hereinafter Hydrate II). Hydrate II exists in the form of crystals having a high aspect ratio, for example, needle-shaped crystals. The water content of these crystals remains substantially constant over a broad relative humidity range (RH about 10–90%). The stable water content of Hydrate II represents an advantage of this crystalline form for use in pharmacy.

There is thus provided in a further aspect of the invention 5-acetamido-2,3,4,5-tetradeoxy-4-guanidino-D-glycero-D-galacto-non-2-enopyranosonic acid in the form of crystals having a low aspect ratio, such as tabular crystals.

DETAILED DESCRIPTION OF PREFERRED EMBODIMENTS

In a further aspect there is provided 5-acetamido-2,3,4,5-tetradeoxy-4guanidino-D-glycero-D-galacto-non-2-enopyranosonic acid in the form of crystals having a high aspect ratio, such as needle-shaped crystals.

Whilst tabular crystals are regarded as typical of Hydrate I and needle-shaped crystals are regarded as typical of Hydrate II, it will be appreciated that the possibility of either Hydrate I or Hydrate II existing in alternative crystal habits under certain circumstances cannot be excluded. It is to be understood that all such alternate crystal habits are within the scope of the present invention.

There is also provided 5-acetamido-2,3,4,5-tetradeoxy-4-guanidino-D-glycero-D-galacto-non-2-enopyranosonic acid in the form of crystals which have stable water content over a broad humidity range, for example RH 10–90%.

Hydrate I loses substantially all of its water of crystallisation at about 80–90° C. Decomposition occurs at 299° C.

Hydrate II loses one mole of water of crystallisation at about 84–90° C. and a further mole of water of crystallisation of about 135–143° C.

In a yet further aspect the invention provides 5-acetamido-2,3,4,5-tetradeoxy-4-guanidino-D-glycero-D-galacto-non-2-enopyranosonic acid in the form of a crystalline hydrate which loses substantially all its water of crystallisation at 80–90° C.

In a yet further aspect the invention provides 5-acetamido-2,3,4,5-tetradeoxy-4-guanidino-D-glycero-D-galacto-non-2-enopyranssonic acid in the form of a crystalling hydrate which loses one mole of water of crystallisation at 84–90° C. and a further mole of water of crystallisation at 135–143° C.

In a preferred aspect the invention provides 5-acetamido-2,3,4,5-tetradeoxy-4-guanidino-D-glycero-D-galacto-non-2-enopyranosonic in the form of Hydrate I as herein defined substantially free of Hydrate II as herein defined.

In a further preferred aspect the invention provides 5acetamido-2,3,4,5-tetradeoxy-4-guanidino-D-glycero-D-galacto-non-2-enopyranosonic acid in the form of Hydrate II as herein defined substantially free of Hydrate I as herein defined.

By "substantially free" is meant containing less than 5% of the alternative hydrate, such as less than 2%, for example less than 1% of the alternative hydrate.

5-Acetamido-2,3,4,5-tetradeoxy-4-guanidino-D-glycero-D-galacto-non-2-enopyranssonic acid may be prepared in crystalline form by crystallisation of the compound from aqueous solution.

Each of Hydrate I and Hydrate II may be prepared substantially free from the alternative Hydrate by controlling the solution concentration and temperature at which crystallisation occurs.

In general, 5-acetamido-2,3,4,5-tetradeoxy-4-guanidino-D-glycero-D-galacto-non-2-enopyranosonic acid in the form of Hydrate I may be obtained by crystallisation of the compound from aqueous solution at a temperature greater than about 50° C., preferably 50–55° C.

In general, 5-acetamido-2,3,4,5-tetradeoxy-4-guanidino-D-glycero-D-galacto-non-2-enopyranosonic acid in the form of Hydrate II may be obtained by crystallisation of the compound from aqueous solution at a temperature below about 40° C., preferably about 20–30° C.

Crystallisation of 5-acetamido-2,3,4,5-tetradeoxy-4-guanidino-D-glycero-D-galacto-non-2-enopyranosonic acid from aqueous solution at a temperature in the range of about 40–50° C. typically results in a mixture of tabular and needle-shaped crystals. Such mixtures are disfavoured for the preparation of pharaceutical formulations because of the differing physical properties of Hydrate I and Hydrate II, in particular their flow properties.

Seeding of an aqueous solution of 5-acetamido-2,3,4,5-tetradeoxy-4-guanidino-D-glycero-D-Galacto-non-2-enopyranosonic acid with crystals of Hydrate I or Hydrate II may lead to crystallisation of the seeded Hydrate. Preparation of Hydrate I or Hydrate II should therefore be conducted in the absence of seeds of the undesired Hydrate. Conversely, Hydrate I may be prepared by seeding an aqueous solution of 5-acetamido-2,3,4,5-tetradeoxy-4-guanidino-D-glycero-D-galacto-non-2-enopyranosonic acid with crystals of Hydrate I, and Hydrate II may be prepared by seeding an aqueous solution of 5-acetamido-2,3,4,5-tetradeoxy-4guanidino-D-glycero-D-galacto-non-2-enopyranosonic acid with crystals of Hydrate II.

For the preparation of Hydrate II it is preferable to employ a relatively dilute aqueous solution, for example a solution of 5-acetamido-2,3,4,5-tetradeoxy-4-guanidino-D-glycero-D-galacto-non-2-enopyranosonic acid in 15–30 volumes of water, for example 20 volumes of water. Hydrate I may conveniently be crystallised from a relatively concentrated aqueous solution, for example a solution of 5-acetamido-2,3,4,5-tetradeoxy-4-guanidino-D-glycero-D-galacto-non-2-enopyranosonic acid in 12–20 volumes of water, such as 12–15 volumes of water.

We have found that Hydrate II may be converted into Hydrate I in aqueous suspension or saturated solution. Such interconversion may be effected by prolonged ageing of an aqueous suspension or saturated solution of Hydrate II, for example ageing for a period of days, for example more than 10 days, such as about 15 days. Alternatively, interconversion may be effected in the presence of a base, for example an organic base such as imidazole.

Recovery of either Hydrate I or Hydrate II from aqueous solution may be enhanced by the addition to the solution of a suitable counter-solvent. Suitable counter-solvents are water-miscible solvents in which the compound of formula (I) has poor solubility. Conveniently the counter-solvent will be a ketone, such as acetone, or an alkanol such as propan-2-ol. A preferred counter-solvent is acetone.

We have also found that addition of an aqueous solution of 5-acetamido-2,3,4,5-tetradeoxy-4-guanidino-D-glycero-D-galacto-non-2-enopyranosonic acid to a similar volume of a counter-solvent as previously deigned results in precipitation of Hydrate II. For example, addition of a solution of 5-acetamido-2,3,4,5-tetradeoxy-4-guanidino-D-glycero-D-galacto-non-2-enopyranosonic acid in 12–15 volumes of water to 12–20 volumes of acetone gives crystals of Hydrate II.

The methods for the preparation of crystalline material, and in particular methods for the preparation of Hydrate I and Hydrate II, described herein constitute further aspects of the present invention.

5-Acetamido-2,3,4,5-tetradeoxy-4-guanidino-D-glycero-D-galacto-non-2-enopyranosonic acid in crystalline form may be used as an antiviral agent as described in WO 91/16320, which is incorporated herein by reference.

5-Acetamido-2,3,4,5-tetradeoxy-4-guanidino-D-glycero-D-galacto-non-2-enopyranosonic acid in crystalline form may be formulated as a pharmaceutical composition for use as an antiviral agent as described in WO 91/16320.

Preferred pharmaceutical formulations of 5-acetamido-2,3,4,5-tetradeoxy-4-guanidino-D-glycero-D-galacto-non-2-enopyranosonic acid include powder formulations and aqueous solutions or suspensions. Preparation of powder formulations requires micronisation of the drug substance. The good flow properties of Hydrate I render it particularly suitable for micronisation. Hydrate II has adequate flow properties and also a particularly rapid dissolution rate in water. These properties render Hydrate II particular advantageous for the preparation of aqueous solution/suspensions.

Hydrates I and II have been subjected to X-ray powder diffraction studies. Diffraction traces were obtained using a Seimens D-500 diffractometer and $CuK_\alpha$ radiation. X-Ray intensities were measured at 0.02° increments for 5 second intervals using a scintillation counter, between values of 5 and 55° 2θ. The d-spacings and line intensities obtained for Hydrate I and Hydrate II are shown in Tables I and II, respectively.

TABLE I

| d(A) | I(%) |
|---|---|
| 10.06 | 30.25 |
| 6.77 | 69.81 |
| 6.63 | 89.61 |
| 6.35 | 12.69 |
| 6.05 | 54.56 |
| 5.38 | 25.11 |
| 5.05 | 98.58 |
| 4.61 | 12.58 |
| 4.42 | 100.00 |
| 4.31 | 8.28 |
| 4.17 | 11.67 |
| 3.98 | 75.00 |
| 3.90 | 52.61 |
| 3.77 | 20.33 |
| 3.69 | 36.17 |
| 3.48 | 26.53 |
| 3.41 | 53.25 |
| 3.37 | 17.61 |
| 3.16 | 18.39 |
| 3.02 | 31.08 |
| 2.98 | 9.25 |
| 2.92 | 6.28 |
| 2.87 | 13.58 |
| 2.82 | 10.78 |
| 2.78 | 6.78 |
| 2.74 | 18.03 |
| 2.69 | 15.33 |
| 2.65 | 6.25 |
| 2.63 | 6.44 |
| 2.59 | 11.44 |
| 2.49 | 14.31 |
| 2.45 | 18.81 |
| 2.41 | 8.64 |
| 2.35 | 11.36 |
| 2.19 | 5.42 |
| 2.13 | 12.25 |
| 2.11 | 6.56 |
| 2.02 | 8.33 |
| 1.98 | 5.47 |

TABLE II

| d(A) | I(%) |
|---|---|
| 16.88 | 66.34 |
| 10.38 | 50.60 |
| 9.50 | 16.08 |
| 8.47 | 40.46 |
| 7.12 | 100.00 |
| 5.84 | 11.78 |
| 5.33 | 18.83 |
| 5.21 | 33.99 |
| 4.78 | 12.94 |
| 4.57 | 75.81 |
| 4.32 | 16.37 |
| 4.25 | 18.49 |
| 4.14 | 43.26 |
| 3.96 | 10.33 |
| 3.76 | 22.11 |
| 3.64 | 25.16 |
| 3.57 | 37.04 |
| 3.52 | 15.69 |
| 3.40 | 16.85 |
| 3.34 | 21.20 |
| 3.17 | 13.52 |
| 3.13 | 17.04 |
| 3.06 | 7.48 |
| 2.94 | 10.19 |
| 2.92 | 8.45 |
| 2.86 | 9.17 |
| 2.76 | 9.56 |
| 2.72 | 9.22 |
| 2.67 | 6.81 |
| 2.64 | 8.06 |
| 2.60 | 5.46 |
| 2.58 | 6.52 |
| 2.51 | 5.31 |
| 2.49 | 6.66 |
| 2.45 | 5.55 |
| 2.43 | 5.89 |
| 2.39 | 15.93 |
| 2.38 | 10.38 |
| 2.31 | 8.40 |
| 2.22 | 5.94 |
| 2.16 | 5.36 |
| 2.11 | 6.28 |
| 2.03 | 7.24 |
| 1.91 | 6.57 |

The following examples illustrate the invention but are not intended as a limitation thereof. All temperatures are in ° C.

EXAMPLE 1

Preparation of Hydrate I

A mixture of 5-acetamido-2,3,4,5-tetradeoxy-4guanidino-D-glycero-D-galacto-non-2-enopyranosonic acid (5.0 g) and water (60 ml) was heated at 100° to give a clear solution. The solution was cooled during 30 min to 55° and maintained at between 55° and 50° during 4 h, to give a crystalline suspension. Acetone (80 ml) was added during 90 min, the temperature being maintained between 48 and 55°. The resultant slurry was stirred 1 h, the temperature being allowed to fall to ca. 20°, and the suspension was allowed to stand 17 h at ambient temperature. The product was collected by vacuum filtration and the filter bed was washed with 4:1 acetone/water (2×10 ml) then with acetone (10 ml). The product was air dried at ambient temperature and humidity to give Hydrate I (tabular crystals) (4.5 g).

PMR ($D_2O$) 2.04 (3H,s), 3.67 (2H,m), 4.23 (1H,m), 4.42 (2H,m), 5.63 (1H,d,J,2.5 Hz)

| | |
|---|---|
| IR (Nujol) | 3248, 3338, 3253; NH, OH 1692, 1666, 1646, 1619, 1575; CO ($CH_3CONH$, $CO_2$), CN |
| Water content | 8.4% w/w; calculated for $C_{12}H_{20}N_4O_7 \cdot 1.7H_2O$ |

EXAMPLE 2

Preparation of Hydrate I

A mixture of 5-acetamido-2,3,4,5-tetradeoxy-4-guanidino-D-glycero-D-galacto-non-2-enopyranosonic acid (15.0 g) and water (180 ml) was heated at 100° to give a clear solution. The solution was clarified by vacuum filtration through a filter paper then cooled to ca. 55° and maintained at between 55° and 50° during 4 h, allowing crystallisation to become established. Acetone (210 ml) was added with stirring, during 2 h, the temperature being maintained at 48–55°. The resultant suspension was stirred and cooled to 30° and was then allowed to stand at ambient temperature 17 h. The solid was filtered and the product was washed with 4:1 acetone/water (2×30 ml) and then acetone (30 ml). The solid was air dried at ambient temperature and humidity to give Hydrate I (tabular crystals) (12.0 g).

Characterisation as above.

EXAMPLE 3

Preparation of Hydrate II

A mixture of 5-acetamido-2,3,4,5-tetradeoxy-4-guanidino-D-glycero-D-galacto-non-2-enopyranosonic acid (10.0 g) and water (100 ml) was heated to 95°. The resultant solution was clarified by vacuum filtration. The solution was then cooled to 30° and acetone (250 ml) was added during 5 min stirring. The resultant thick white suspension was allowed to stand at ambient temperature 20 h. The solid was collected by vacuum filtration and was washed with 4:1 acetone/water (2×20 ml) then with acetone (20 ml). The solid was dried in a vacuum oven at 35° for 24 h and then equilibrated with atmospheric moisture at ambient temperature and humidity to give Hydrate II (needle-shaped crystals) (8.16 g).

Characterisation as above.

Water content 10.6% w/w; calculated for $C_{12}H_{20}N_4O_7 \cdot 2H_2O$ 9.8% w/w.

EXAMPLE 4

Preparation of Hydrate II

A mixture of 5-acetamido-2,3,4,5-tetradeoxy-4-guanidino-D-glycero-D-galacto-non-2-enopyranosonic acid (10.0 g) and water (400 ml) was heated to 20° for 2 h. The resultant solution was clarified by vacuum filtration. Acetone (110 ml) was added and solid began to crystallise. The resultant suspension was stirred for 2.5 h at 20°. The solid was collected by vacuum filtration and was washed with 4:1 v/v acetone/water (2×20 ml) then with acetone (20 ml). The solid was dried in a vacuum oven at 30° and then equilibrated with atmospheric moisture at ambient temperature and humidity to give Hydrate II (needle-shaped crystals) (7.7 g)

Characterisation as above.

Water content 11.1% w/w calculated for $C_{12}H_{20}N_4O_7 \cdot 2H_2O$ 9.8 w/w.

EXAMPLE 5

Preparation of Hydrate II

A mixture of 5-acetamido-2,3,4,5-tetradeoxy-4-guanidino-D-glycero-D-galacto-non-2-eno-pyranosonic acid (50 g) and water (1150 ml) was heated to 75°. The resultant solution was clarified by vacuum filtration, washing through with water (100 ml). The solution was then cooled to 7° over 1 h and aceton (500 ml) was added. The resultant solution was stirred slowly for 0.5 h, during which time solid began to crystallise. Acetone (750 ml) was then added to the suspension over 2 h, maintaining the temperature at 5–10°. The solid was collected by vacuum filtration and washed with 4:1 v/v acetone/water (2×100 ml) then with acetone (100 ml). The solid was air-dried at ambient temperature and humidity to give Hydrate II (needle-shaped crystals) (46.0 g).

Water content 9.8% w/w; calculated for $C_{12}H_{20}N_4O_7 \cdot 2H_2O$ 9.8% w/w.

XRD: consistent with Hydrate II (>Pb 99%).

EXAMPLE 6

Precipitation of Hydrate II

A mixture of 5-acetamido-2,3,4,5-tetradeoxy-4-guanidino-D-glycero-D-galacto-non-2-eno-pyranosonic acid (50 g) and water (600 ml) was heated to 100°. The resultant clear hot solution was added over 8 minutes to acetone (700 ml) stirred rapidly at ambient temperature, causing the temperature of the mixture to rise from 20° to 56° and precipitation of solid. The resultant suspension was allowed to cool to 20° with stirring, then the solid was collected by vacuum filtration and washed with 4:1 acetone/water (2×100 ml) then with acetone (100 ml). The solid was air-dried at ambient temperature and humidity to give Hydrate II (needle-shaped crystals) (47.9 g).

Water content 10.0 w/w; calculated for $C_{12}H_{20}N_4O_7 \cdot 2H_2O$ 9.8% w/w.

XRD: consistent with Hydrate II (>99%).

EXAMPLE 7

Crystallisation of Hydrate I from Water

A mixture of 5-acetamido-2,3,4,5-tetradeoxy-4-guanidino-D-glycero-D-galacto-non-2-eno-pyranosonic acid (35.7 g) and water (350 ml) was heated at 95° to give a clear solution. This was adjusted to pH7.0 (from pH6.4) with aqueous acetic acid (100 µl, 10% v/v). The resulting solution was allowed to cool to ambient temperature with stirring, to give a crystalline suspension. The product was collected by vacuum filtration, then vacuum-dried at ambient temperature to give Hydrate I (tabular crystals) (28.9 g).

IR consistent with Hydrate I

EXAMPLE 8

Preparation of Hydrate II by Seeding

A mixture of 5-acetamido-2,3,4,5-tetradeoxy-4guanidino-D-glycero-D-galacto-non-2-eno-pyranosonic acid (30.0 g) and water (540 ml) was heated at 75° to give a solution. The resultant solution was clarified by vacuum filtration, washing through with water (54 ml). The solution was heated to 100°, cooled to 40°, then seeded with Hydrate II (0.3 ). Crystallisation occurred as the temperature was further reduced to ambient temperature. The resultant slurry was stirred for 1 h at ambient temperature, cooled to 5°, then acetone (600 ml) was added over 1.5 h. The solid was collected by vacuum filtration and washed with 4:1 v/v acetone/water (2×60 ml) then with acetone (60 ml). The solid was air-dried at ambient temperature and humidity to give Hydrate II (needle-shaped crystals) (26.5 g).

XRD 90–95% Hydrate II (5–10% Hydrate I)

EXAMPLE 9

Interconversion of Hydrate II to Hydrate I by Ageing

A mixture of 5-acetamidon-2,3,4,5-tetradeoxy-4-guanidino-D-glycero-D-galacto-non-2-eno-pyranosonic acid (10.0 g) and water (200 ml) was heated at 100° to give a solution. The resultant solution was rapidly cooled to 30°, seeded with Hydrate II (0.05 g) then left unstirred overnight. Light-microscopy showed exclusively the characteristic needles of Hydrate II. The suspension was aged unstirred at ambient temperature for 11 days (when light-microscopy showed the presence of some crystals of Hydrate I), then stirred for 3 days. Acetone (200 ml) was added, and the slurry was stirred for 1 h. the solid was collected by vacuum filtration and washed with 4:1 v/v acetone/water (2×20 ml) then with acetone (20 ml). The solid was air-dried at ambient temperature and humidity to give Hydrate I (tabular crystals) (9.0 g).

XRD: Consistent with Hydrate I >99%)

EXAMPLE 10

Interconversion of Hydrate II to Hydrate I using Base

A suspension of 5-acetamido-2,3,4,5-tetradeoxy-4-guanidino-D-glycero-D-galacto-non-2-enopyranosonic acid (5.0 g, Hydrate II) in water (30 ml), containing imidazole (2.96 g) was stirred and heated at 30° for 40 h. The remaining solid was collected by vacuum filtration and washed with water (2×1 ml, 2×5 ml) then air-dried at ambient temperature and humidity to give Hydrate I (tabular crystals) (3.98 g).

IR consistent with Hydrate I

EXAMPLE 11

Preparation of Hydrate I by Seeding

A mixture of 5-acetamido-2,3,4,5-tetradeoxy-4-guanidino-D-glycero-D-galacto-non-2-eno-pyranosonic acid (5.0 g) and water (60 ml) was heated at 100° to give a solution. The resultant solution was clarified by vacuum filitration. The resultant solution was cooled to about 50°, seeded with Hydrate I, left unstirred at 50–55° for 1 h, then stirred for 1 h at 50–55°. Acetone (70 ml) was added whilst a temperature of 48–55° was maintained. The slurry was stirred for 1 h at 50–55°, then aged unstirred overnight at ambient temperature. The solid was collected by vacuum filtration and washed with 4:1 v/v acetone/water (2×10 ml) then with acetone (2×10 ml). The solid was vacuum-dried, then allowed to re-equilibrate at ambient temperature and humidity to give Hydrate I (tabular crystals) (3.8 g).

XRD: Consistant with Hydrate I (>99%)

What is claimed is:

1. 5-Acetamido-2,3,4,5-tetradeoxy-4-guanidino-D-glycero-D-galacto-non-2-enopyranoasonic acid in crystalline hydrate form, wherein the crystals have a low aspect ratio and an X-ray diffraction trace having the line intensities at the indicated d-spacings essentially as shown:

| d(A) | I(%) |
|---|---|
| 10.06 | 30.25 |
| 6.77 | 69.81 |
| 6.63 | 89.61 |
| 6.35 | 12.69 |
| 6.05 | 54.56 |
| 5.38 | 25.11 |
| 5.05 | 98.58 |
| 4.61 | 12.58 |
| 4.42 | 100.00 |
| 4.31 | 8.28 |
| 4.17 | 11.67 |
| 3.98 | 75.00 |
| 3.90 | 52.61 |
| 3.77 | 20.33 |
| 3.69 | 36.17 |
| 3.48 | 26.53 |
| 3.41 | 53.25 |
| 3.37 | 17.61 |
| 3.16 | 18.39 |
| 3.02 | 31.08 |
| 2.98 | 9.25 |
| 2.92 | 6.28 |
| 2.87 | 13.58 |
| 2.82 | 10.78 |
| 2.78 | 6.78 |
| 2.74 | 18.03 |
| 2.69 | 15.33 |
| 2.65 | 6.25 |
| 2.63 | 6.44 |
| 2.59 | 11.44 |
| 2.49 | 14.31 |
| 2.45 | 18.81 |
| 2.41 | 8.64 |
| 2.35 | 11.36 |
| 2.19 | 5.42 |
| 2.13 | 12.25 |
| 2.11 | 6.56 |
| 2.02 | 8.33 |
| 1.98 | 5.47, | or wherein the crystals have a high aspect ratio and an X-ray diffraction trace having the line intensities at the indicated d-spacings essentially as shown:

| d(A) | I(%) |
|---|---|
| 16.88 | 66.34 |
| 10.38 | 50.60 |
| 9.50 | 16.08 |
| 8.47 | 40.46 |
| 7.12 | 100.00 |
| 5.84 | 11.78 |
| 5.33 | 18.83 |
| 5.21 | 33.99 |
| 4.78 | 12.94 |
| 4.57 | 75.81 |
| 4.32 | 16.37 |
| 4.25 | 18.49 |
| 4.14 | 43.26 |
| 3.96 | 10.33 |
| 3.76 | 22.11 |
| 3.64 | 25.16 |
| 3.57 | 37.04 |
| 3.52 | 15.69 |
| 3.40 | 16.85 |
| 3.34 | 21.20 |
| 3.17 | 13.52 |
| 3.13 | 17.04 |
| 3.06 | 7.48 |
| 2.94 | 10.19 |
| 2.92 | 8.45 |
| 2.86 | 9.17 |
| 2.76 | 9.56 |
| 2.72 | 9.22 |
| 2.67 | 6.81 |
| 2.64 | 8.06 |
| 2.60 | 5.46 |
| 2.58 | 6.52 |
| 2.51 | 5.31 |
| 2.49 | 6.66 |
| 2.45 | 5.55 |
| 2.43 | 5.89 |
| 2.39 | 15.93 |
| 2.38 | 10.38 |
| 2.31 | 8.40 |
| 2.22 | 5.94 |
| 2.16 | 5.36 |
| 2.11 | 6.28 |
| 2.03 | 7.24 |
| 1.91 | 6.57. |

2. 5-Acetamido-2,3,4,5-tetradeoxy-4-guanidino-D-glycero-D-galacto-non-2-enopyranosonic acid according to claim 1, in the form of crystals having a low aspect ratio.

3. The crystalline hydrate form as claimed in claim 2, wherein the hydrate crystals are tabular.

4. The crystalline hydrate form as claimed in claim 2, wherein substantially all water of crystallization is lost at about 80 to 90° C.

5. 5-Acetamido-2,3,4,5-tetradeoxy-4-guanidino-D-glycero-D-galacto-non-2-enopyramosonic acid according to claim 1, in the form of dihydrate crystals having a high aspect ratio.

6. The crystalline dihydrate form as claimed in claim 5, wherein the dihydrate crystals are needle-shaped.

7. The crystalline dihydrate form as claimed in claim 5, wherein water content is stable over a broad range of relative humidity.

8. The crystalline dihydrate form as claimed in claim 5, wherein one mole of water of crystallization is lost by about 135–143° C.

9. The crystalline hydrate of claim 1, wherein the crystalline hydrate is substantially free of the crystalline hydrate form having a high aspect ratio.

10. The crystalline hydrate of claim 1, wherein the crystalline hydrate is substantially free of the crystalline hydrate form having a low aspect ratio.

11. 5-Acetamido-2,3,4,5-tetradeoxy-4-guanidino-D-glycero-D-galacto-non-2-enopyramosonic acid as claimed in claim 1, in micronized form.

12. A pharmaceutical formulation comprising 5-acetamido-2,3,4,5-tetradeoxy-4-guanidino-D-glycero-D-galacto-non-2-enopyramosonic acid in crystalline hydrate form, and a pharmaceutically acceptable carrier therefor, wherein the crystals have a low aspect ratio and an X-ray diffraction trace having the line intensities at the indicated d-spacings essentially as shown:

| d(A) | I(%) |
|---|---|
| 10.06 | 30.25 |
| 6.77 | 69.81 |
| 6.63 | 89.61 |

-continued

| d(A) | I(%) |
|---|---|
| 6.35 | 12.69 |
| 6.05 | 54.56 |
| 5.38 | 25.11 |
| 5.05 | 98.58 |
| 4.61 | 12.58 |
| 4.42 | 100.00 |
| 4.31 | 8.28 |
| 4.17 | 11.67 |
| 3.98 | 75.00 |
| 3.90 | 52.61 |
| 3.77 | 20.33 |
| 3.69 | 36.17 |
| 3.48 | 26.53 |
| 3.41 | 53.25 |
| 3.37 | 17.61 |
| 3.16 | 18.39 |
| 3.02 | 31.08 |
| 2.98 | 9.25 |
| 2.92 | 6.28 |
| 2.87 | 13.58 |
| 2.82 | 10.78 |
| 2.78 | 6.78 |
| 2.74 | 18.03 |
| 2.69 | 15.33 |
| 2.65 | 6.25 |
| 2.63 | 6.44 |
| 2.59 | 11.44 |
| 2.49 | 14.31 |
| 2.45 | 18.81 |
| 2.41 | 8.64 |
| 2.35 | 11.36 |
| 2.19 | 5.42 |
| 2.13 | 12.25 |
| 2.11 | 6.56 |
| 2.02 | 8.33 |
| 1.98 | 5.47, | or wherein the crystals have a high aspect ratio and an X-ray diffraction trace having the line intensities at the indicated d-spacings essentially as shown:

| d(A) | I(%) |
|---|---|
| 16.88 | 66.34 |
| 10.38 | 50.60 |
| 9.50 | 16.08 |
| 8.47 | 40.46 |
| 7.12 | 100.00 |
| 5.84 | 11.78 |
| 5.33 | 18.83 |
| 5.21 | 33.99 |
| 4.78 | 12.94 |
| 4.57 | 75.81 |
| 4.32 | 16.37 |
| 4.25 | 18.49 |
| 4.14 | 43.26 |
| 3.96 | 10.33 |
| 3.76 | 22.11 |
| 3.64 | 25.16 |
| 3.57 | 37.04 |
| 3.52 | 15.69 |
| 3.40 | 16.85 |
| 3.34 | 21.20 |
| 3.17 | 13.52 |
| 3.13 | 17.04 |
| 3.06 | 7.48 |
| 2.94 | 10.19 |
| 2.92 | 8.45 |
| 2.86 | 9.17 |
| 2.76 | 9.56 |
| 2.72 | 9.22 |
| 2.67 | 6.81 |
| 2.64 | 8.06 |

-continued

| d(A) | I(%) |
|---|---|
| 2.60 | 5.46 |
| 2.58 | 6.52 |
| 2.51 | 5.31 |
| 2.49 | 6.66 |
| 2.45 | 5.55 |
| 2.43 | 5.89 |
| 2.39 | 15.93 |
| 2.38 | 10.38 |
| 2.31 | 8.40 |
| 2.22 | 5.94 |
| 2.16 | 5.36 |
| 2.11 | 6.28 |
| 2.03 | 7.24 |
| 1.91 | 6.57. |

13. A pharmaceutical formulation as claimed in claim 12, in the form of a powder.

14. A pharmaceutical formulation comprising 5-acetamido-2,3,4,5-tetradeoxy-4-guanidino-D-glycero-D-galacto-non-2-enopyranosonic acid as claimed in claim 1, in micronized form, and a pharmaceutically acceptable carrier therefor.

15. A method for the preparation of 5-acetamido-2,3,4,5-tetradeoxy-4-guanidino-D-glycero-D-galacto-non-2-enopyranosonic acid in crystalline hydrate form, which method comprises crystallization of 5-acetamido-2,3,4,5-tetradeoy-4-guanidino-D-glycero-D-galacto-non-2-enopyranosonic acid from aqueous solution, wherein the crystals have a low aspect ratio and an X-ray diffraction trace having the line intensities at the indicated d-spacing essentially as shown:

| d(A) | I(%) |
|---|---|
| 10.06 | 30.25 |
| 6.77 | 69.81 |
| 6.63 | 89.61 |
| 6.35 | 12.69 |
| 6.05 | 54.56 |
| 5.38 | 25.11 |
| 5.05 | 98.58 |
| 4.61 | 12.58 |
| 4.42 | 100.00 |
| 4.31 | 8.28 |
| 4.17 | 11.67 |
| 3.98 | 75.00 |
| 3.90 | 52.61 |
| 3.77 | 20.33 |
| 3.69 | 36.17 |
| 3.48 | 26.53 |
| 3.41 | 53.25 |
| 3.37 | 17.61 |
| 3.16 | 18.39 |
| 3.02 | 31.08 |
| 2.98 | 9.25 |
| 2.92 | 6.28 |
| 2.87 | 13.58 |
| 2.82 | 10.78 |
| 2.78 | 6.78 |
| 2.74 | 18.03 |
| 2.69 | 15.33 |
| 2.65 | 6.25 |
| 2.63 | 6.44 |
| 2.59 | 11.44 |
| 2.49 | 14.31 |
| 2.45 | 18.81 |
| 2.41 | 8.64 |
| 2.35 | 11.36 |

-continued

| d(A) | I(%) |
|---|---|
| 2.19 | 5.42 |
| 2.13 | 12.25 |
| 2.11 | 6.56 |
| 2.02 | 8.33 |
| 1.98 | 5.47, | or wherein the crystals have a high aspect ratio and an X-ray diffraction trace having the line intensities at the indicated d-spacings essentially as shown:

| d(A) | I(%) |
|---|---|
| 16.88 | 66.34 |
| 10.38 | 50.60 |
| 9.50 | 16.08 |
| 8.47 | 40.46 |
| 7.12 | 100.00 |
| 5.84 | 11.78 |
| 5.33 | 18.83 |
| 5.21 | 33.99 |
| 4.78 | 12.94 |
| 4.57 | 75.81 |
| 4.32 | 16.37 |
| 4.25 | 18.49 |
| 4.14 | 43.26 |
| 3.96 | 10.33 |
| 3.76 | 22.11 |
| 3.64 | 25.16 |
| 3.57 | 37.04 |
| 3.52 | 15.69 |
| 3.40 | 16.85 |
| 3.34 | 21.20 |
| 3.17 | 13.52 |
| 3.13 | 17.04 |
| 3.06 | 7.48 |
| 2.94 | 10.19 |
| 2.92 | 8.45 |
| 2.86 | 9.17 |
| 2.76 | 9.56 |
| 2.72 | 9.22 |
| 2.67 | 6.81 |
| 2.64 | 8.06 |
| 2.60 | 5.46 |
| 2.58 | 6.52 |
| 2.51 | 5.31 |
| 2.49 | 6.66 |
| 2.45 | 5.55 |
| 2.43 | 5.89 |
| 2.39 | 15.93 |
| 2.38 | 10.38 |
| 2.31 | 8.40 |
| 2.22 | 5.94 |
| 2.16 | 5.36 |
| 2.11 | 6.28 |
| 2.03 | 7.24 |
| 1.91 | 6.57. |

16. A method as claimed in claim 15, for the preparation of a crystalline hydrate of said compound having a low aspect ratio.

17. A method as claimed in claim 16, wherein the temperature of the aqueous solution is greater than about 50° C.

18. A method as claimed in claim 17, wherein the temperature of the aqueous solution is in the range of 50 to 55° C.

19. A method as claimed in claim 16, wherein the aqueous solution is seeded with crystals of the crystalline hydrate form having a low aspect ratio.

20. A method as claimed in claim 15, for the preparation of the crystalline dihydrate form having a high aspect ratio.

21. A method as claimed in claim 20, wherein the temperature of the aqueous solution is less than about 40° C.

22. A method as claimed in claim 21, wherein the temperature of the aqueous solution is in the range 20 to 30° C.

23. A method as claimed in claim 20, wherein the aqueous solution is seeded with crystals of the crystalline dihydrate form having a high aspect ratio.

24. A method as claimed in claim 15, comprising the step of addition of a counter solvent to the aqueous solution.

25. A method as claimed in claim 24, wherein the counter solvent is a ketone or an alkanol.

26. A method as claimed in claim 25, wherein the counter solvent is acetone.

27. A method for the preparation of the crystalline hydrate form as claimed in claim 2, which method comprises interconversion of the crystalline dihydrate form having a high aspect ratio.

28. The method as claimed in claim 27, wherein interconversion is effected by aging of the aqueous solution.

29. The method as claimed in claim 27, wherein the interconversion is effected by addition of a base to the aqueous solution.

30. A method for the preparation of the crystalline dihydrate form as claimed in claim 5, which process comprises addition of an aqueous solution of 5-acetamido-2,3,4,5-tetradeoxy-4-guanidino-D-glycero-D-galacto-non-2-enopyranosonic acid to a similar volume of a counter solvent.

31. The method as claimed in claim 30, wherein the counter solvent is acetone.

32. A method for the preparation of the pharmaceutical formulation in the form of an aqueous solution or suspension, which method comprises dissolution in water of crystalline hydrate of 5-acetamido-2,3,4,5-tetradeoxy-4-guanidino-D-glycero-D-galacto-non-2-enopyranosonic acid, wherein the crystals have a low aspect ratio and an X-ray diffraction trace having the line intensities at the indicated d-spacings essentially as shown:

| d(A) | I(%) |
|---|---|
| 10.06 | 30.25 |
| 6.77 | 69.81 |
| 6.63 | 89.61 |
| 6.35 | 12.69 |
| 6.05 | 54.56 |
| 5.38 | 25.11 |
| 5.05 | 98.58 |
| 4.61 | 12.58 |
| 4.42 | 100.00 |
| 4.31 | 8.28 |
| 4.17 | 11.67 |
| 3.98 | 75.00 |
| 3.90 | 52.61 |
| 3.77 | 20.33 |
| 3.69 | 36.17 |
| 3.48 | 26.53 |
| 3.41 | 53.25 |
| 3.37 | 17.61 |
| 3.16 | 18.39 |
| 3.02 | 31.08 |
| 2.98 | 9.25 |
| 2.92 | 6.28 |
| 2.87 | 13.58 |
| 2.82 | 10.78 |
| 2.78 | 6.78 |
| 2.74 | 18.03 |
| 2.69 | 15.33 |
| 2.65 | 6.25 |
| 2.63 | 6.44 |

-continued

| d(A) | I(%) |
|---|---|
| 2.59 | 11.44 |
| 2.49 | 14.31 |
| 2.45 | 18.81 |
| 2.41 | 8.64 |
| 2.35 | 11.36 |
| 2.19 | 5.42 |
| 2.13 | 12.25 |
| 2.11 | 6.56 |
| 2.02 | 8.33 |
| 1.98 | 5.47, | or wherein the crystals have a high aspect ratio and an X-ray diffraction trace having the line intensities at the indicated d-spacings essentially as shown:

| d(A) | I(%) |
|---|---|
| 16.88 | 66.34 |
| 10.38 | 50.60 |
| 9.50 | 16.08 |
| 8.47 | 40.46 |
| 7.12 | 100.00 |
| 5.84 | 11.78 |
| 5.33 | 18.83 |
| 5.21 | 33.99 |
| 4.78 | 12.94 |
| 4.57 | 75.81 |
| 4.32 | 16.37 |
| 4.25 | 18.49 |
| 4.14 | 43.26 |

-continued

| d(A) | I(%) |
|---|---|
| 3.96 | 10.33 |
| 3.76 | 22.11 |
| 3.64 | 25.16 |
| 3.57 | 37.04 |
| 3.52 | 15.69 |
| 3.40 | 16.85 |
| 3.34 | 21.20 |
| 3.17 | 13.52 |
| 3.13 | 17.04 |
| 3.06 | 7.48 |
| 2.94 | 10.19 |
| 2.92 | 8.45 |
| 2.86 | 9.17 |
| 2.76 | 9.56 |
| 2.72 | 9.22 |
| 2.67 | 6.81 |
| 2.64 | 8.06 |
| 2.60 | 5.46 |
| 2.58 | 6.52 |
| 2.51 | 5.31 |
| 2.49 | 6.66 |
| 2.45 | 5.55 |
| 2.43 | 5.89 |
| 2.39 | 15.93 |
| 2.38 | 10.38 |
| 2.31 | 8.40 |
| 2.22 | 5.94 |
| 2.16 | 5.36 |
| 2.11 | 6.28 |
| 2.03 | 7.24 |
| 1.91 | 6.57. |

\* \* \* \* \*